(12) United States Patent
Iwata et al.

(10) Patent No.: US 11,510,568 B2
(45) Date of Patent: Nov. 29, 2022

(54) FUNDUS IMAGING APPARATUS

(71) Applicant: NIDEK CO., LTD., Aichi (JP)

(72) Inventors: Shinya Iwata, Aichi (JP); Megumi Tsuchiya, Aichi (JP); Yukihiro Higuchi, Aichi (JP)

(73) Assignee: NIDEK CO., LTD., Aichi (JP)

( * ) Notice: Subject to any disclaimer, the term of this patent is extended or adjusted under 35 U.S.C. 154(b) by 430 days.

(21) Appl. No.: 16/780,123

(22) Filed: Feb. 3, 2020

(65) Prior Publication Data

US 2020/0288974 A1    Sep. 17, 2020

(30) Foreign Application Priority Data

Feb. 4, 2019  (JP) .............................. JP2019-018331
Jan. 31, 2020 (JP) .............................. JP2020-014526

(51) Int. Cl.
 *A61B 3/12* (2006.01)
 *A61B 3/10* (2006.01)

(52) U.S. Cl.
 CPC ............ *A61B 3/1225* (2013.01); *A61B 3/102* (2013.01)

(58) Field of Classification Search
 CPC .......... A61B 3/1225; A61B 3/102; A61B 3/12
 USPC ....................................................... 351/206
 See application file for complete search history.

(56) References Cited

U.S. PATENT DOCUMENTS

2018/0303334 A1* 10/2018 Tokuyama ........... A61B 3/0041
2020/0000335 A1*  1/2020 Yoshino .................... G06T 5/50

FOREIGN PATENT DOCUMENTS

EP        3235421 A1 * 10/2017 .......... A61B 3/1025
JP      2018-201742 A   12/2018

* cited by examiner

*Primary Examiner* — Mohammed A Hasan
(74) *Attorney, Agent, or Firm* — Sughrue Mion, PLLC

(57) ABSTRACT

A fundus imaging apparatus includes an imaging optical system that irradiates a fundus of a subject eye with light through an objective lens system, and enables to capture a fundus image of the subject eye based on return light from the subject eye, and a diopter correction unit that includes an optical element disposed on an optical path of the imaging optical system and a drive unit driving the optical element, and performs a diopter correction with a diopter value corresponding to a drive amount of the optical element. A drive range of the optical element in the diopter correction unit is set to avoid a specific range being a range in which an artifact caused by reflection light in the objective lens system is maximized.

12 Claims, 6 Drawing Sheets

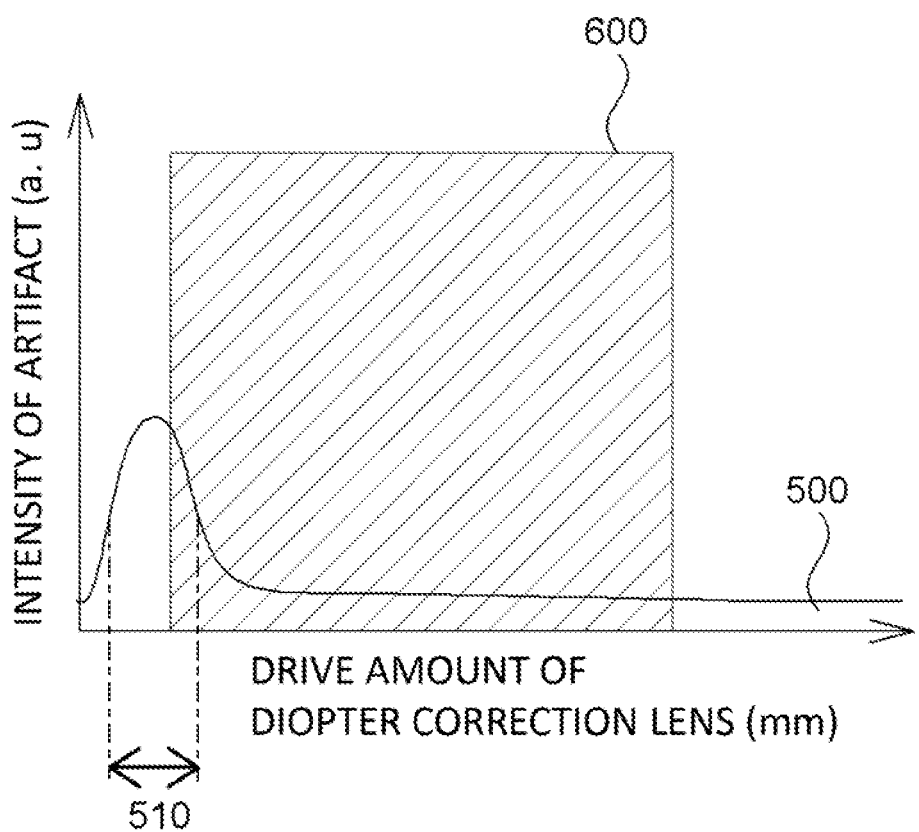

FUNDUS IMAGING APPARATUS

CROSS-REFERENCE TO RELATED APPLICATION

This application claims priority from Japanese Patent Applications No. 2019-018331 filed on Feb. 4, 2019 and No. 2020-014526 filed on Jan. 31, 2020, the entire subject-matter of which is incorporated herein by reference.

TECHNICAL FIELD

The present disclosure relates to a fundus imaging apparatus obtaining a fundus image of a subject eye.

BACKGROUND

In the related art, there is an apparatus that captures a fundus image of a subject eye. For example, there is an apparatus having an objective optical system using a lens system (refraction system), in which both of irradiation of the fundus with illumination light and reception of return light from the fundus are performed through the objective optical system, and thus a fundus image is captured.

JP-A-2018-201742 discloses a fundus imaging apparatus having a diopter correction unit. An optical element included in the diopter correction unit is controlled to be driven according to the diopter of a subject eye such that a diopter correction is performed, and an imaging surface of the apparatus is conjugate to the fundus.

In a case where a diopter value is a value at which the imaging surface of the apparatus is conjugate to a lens surface of an objective optical system, a value at which the imaging surface of the apparatus is conjugate to a curvature central face of the lens surface of the objective optical system, and a value around the value, an artifact caused by reflection at the lens surface tends to occur on a fundus image. Particularly, in an apparatus having a larger angle of view, the artifact tends to be problematic. As a range of a diopter value (D) that is correctable in the apparatus becomes wider, the artifact tends to become more problematic.

SUMMARY

An object of the present disclosure is to provide a fundus imaging apparatus that enables to favorably capture a fundus image.

According to the present disclosure, there is provided a fundus imaging apparatus including an imaging optical system that irradiates a fundus of a subject eye with light through an objective lens system, and enables to capture a fundus image of the subject eye based on return light from the subject eye, and a diopter correction unit that includes an optical element disposed on an optical path of the imaging optical system and a drive unit driving the optical element, and performs a diopter correction with a diopter value corresponding to a drive amount of the optical element, in which a drive range of the optical element in the diopter correction unit is set to avoid a specific range being a range in which an artifact caused by reflection light in the objective lens system is maximized.

BRIEF DESCRIPTION OF DRAWINGS

FIG. 3A is a graph showing a relationship between a drive range of an optical element in a diopter correction unit and an artifact in a retreated state.

DETAILED DESCRIPTION

<Outline>

Hereinafter, with reference to the drawings, an embodiment of a fundus imaging apparatus according to the present disclosure will be described.

Figure 1:
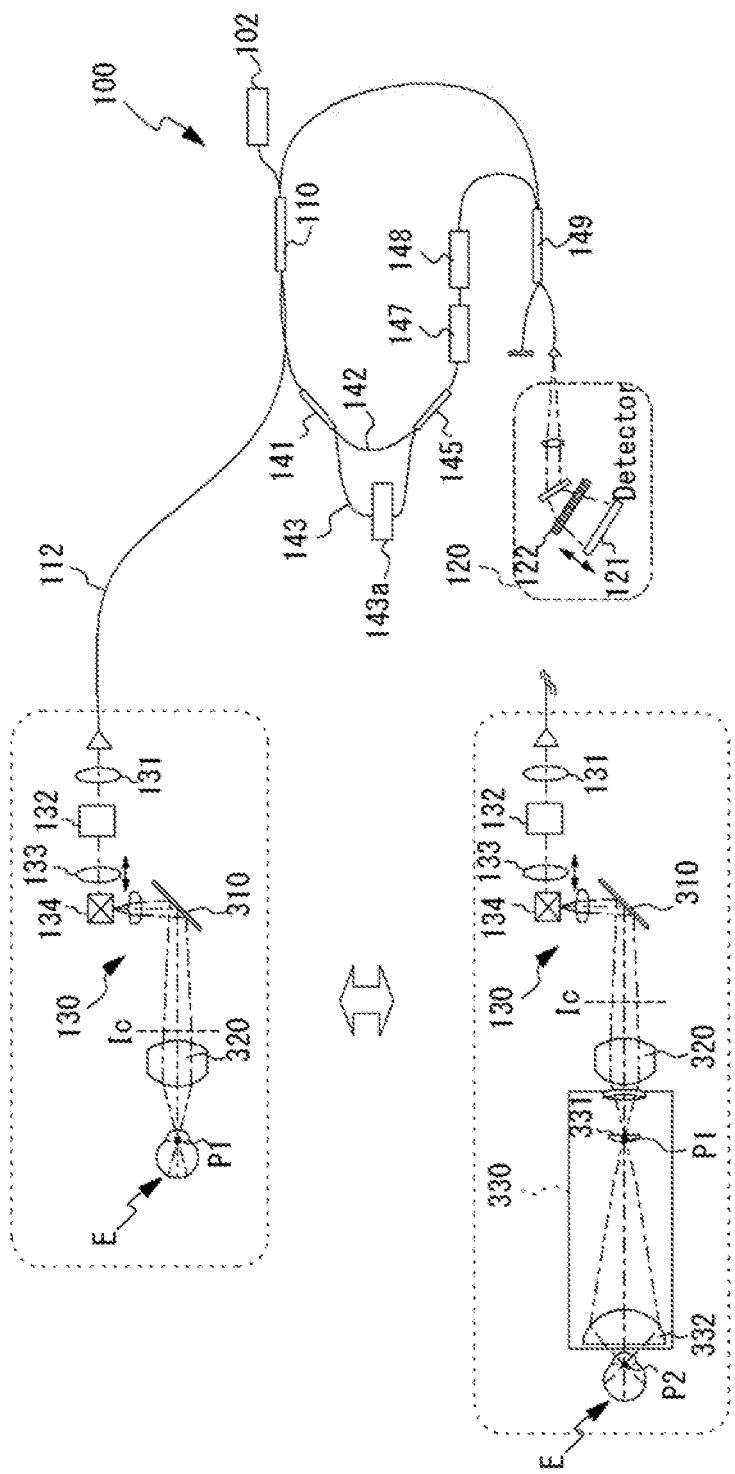
FIG. 1 is a diagram illustrating an example of an optical system of an OCT apparatus according to the present example.
Figure 2:
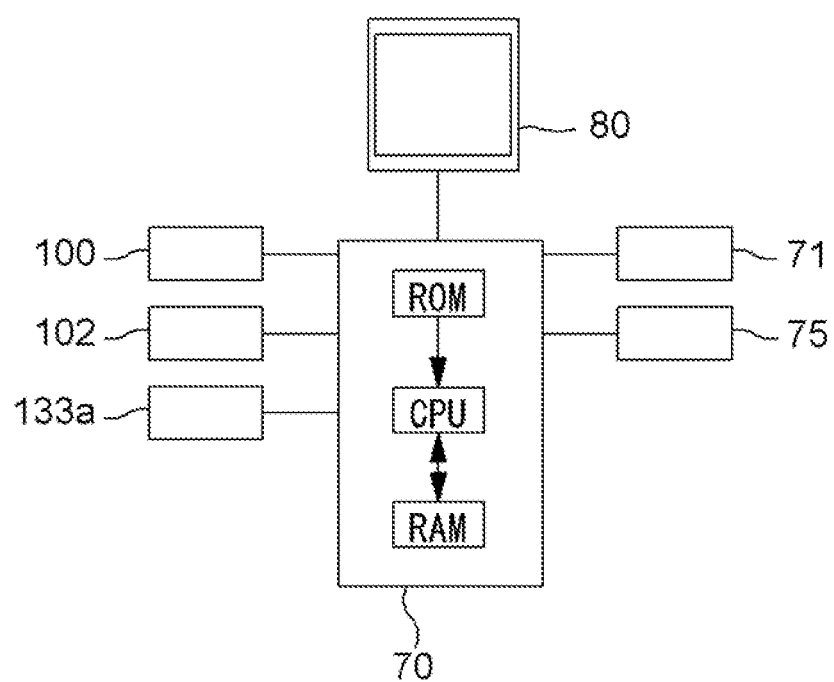
FIG. 2 is a diagram illustrating an example of a control system of the OCT apparatus according to the present example.

The fundus imaging apparatus includes at least an imaging optical system (refer to FIG. 1) and a diopter correction unit (refer to FIGS. 1 and 2). The fundus imaging apparatus may further include an angle-of-view switching unit and a control unit (refer to FIG. 2).

In the present embodiment, the imaging optical system enables to capture a fundus image.

The imaging optical system irradiates the fundus of a subject eye with light from a light source through an objective lens system, and captures a fundus image of the subject eye based on return light from the fundus. The imaging optical system may have a light receiving element that receives the return light from the fundus, and may acquire a fundus image based on a signal from the light receiving element. The imaging optical system may include a front imaging optical system, may include an OCT optical system (refer to FIG. 1), and may include both thereof. The front imaging optical system captures a front image of the fundus. The OCT optical system acquires OCT data of the fundus based on a spectrum interference signal between the return light and reference light. In the present embodiment, in a case where the imaging optical system includes both of the front imaging optical system and the OCT optical system, the objective lens system is shared by the front imaging optical system and the OCT optical system. The objective lens system is an objective optical system in the fundus imaging apparatus, and forms an exit pupil on the anterior ocular segment of the subject eye. The objective lens system has one or more lenses.

<Diopter Correction Unit>

The diopter correction unit is used for a diopter correction in the imaging optical system. The diopter correction unit includes optical elements (a lens, a prism, and the like) and a drive unit. The optical elements are disposed on an optical path of the imaging optical system. The drive unit drives the optical elements. The diopter correction is performed with a diopter value corresponding to a drive amount of the optical elements. When the optical elements are driven, a conjugate position being a position conjugate to an imaging surface of the apparatus and formed with respect to at least the diopter correction unit is displaced.

In the following description, unless otherwise mentioned, the drive unit is assumed to include an actuator used for drive control of the optical elements. However, this is only an example. For example, the drive unit may include a mechanical mechanism that displaces the optical element in response to an examiner's operation instead of the actuator.

Any of various known optical systems may be applied to the diopter correction unit. For example, an optical system changing a positional relationship between optical elements or an optical system having a variable focus lens is known as the diopter correction unit.

<Artifact Occurring Due to Objective Lens System>

Light is reflected at a lens surface of the objective lens system while the light is guided to the fundus from a light source. In a case where reflection light at the lens surface is received by a light receiving element without being removed, an artifact occurs on a fundus image. For example, in addition to an artifact (also referred to as a ghost) caused by reflection light from a center region of an objective lens, there is an artifact caused by light reflected at dust attached to the lens surface or a fine scratch of the lens surface.

As a conjugate position to the imaging surface of the apparatus with respect to the diopter correction unit, the conjugate position being near the objective lens system, comes closer to the lens surface or comes closer to a curvature central face of the lens surface, an artifact tends to occur. In other words, the intensity of the artifact increases. Particularly, when the conjugate position matches one of the lens surface of the objective lens system or the curvature central face, or is located in the vicinity thereof, an intensity peak of the artifact is generated. In other words, in a graph (for example, refer to FIGS. 3A, 3B, and 5) having a drive amount of the optical element in the diopter correction unit as a transverse axis and the intensity of the artifact as a longitudinal axis, a peak portion (a specific range in the present embodiment) is formed at a value at which the conjugate position matches one of lens surfaces of the objective lens system, the conjugate position matches one of curvature central faces of the lens surfaces, or a value around the value. Particularly, in a case where saturation as illustrated in FIGS. 3B and 5 occurs, the influence on image quality is great in a range thereof.

Figure 3B:
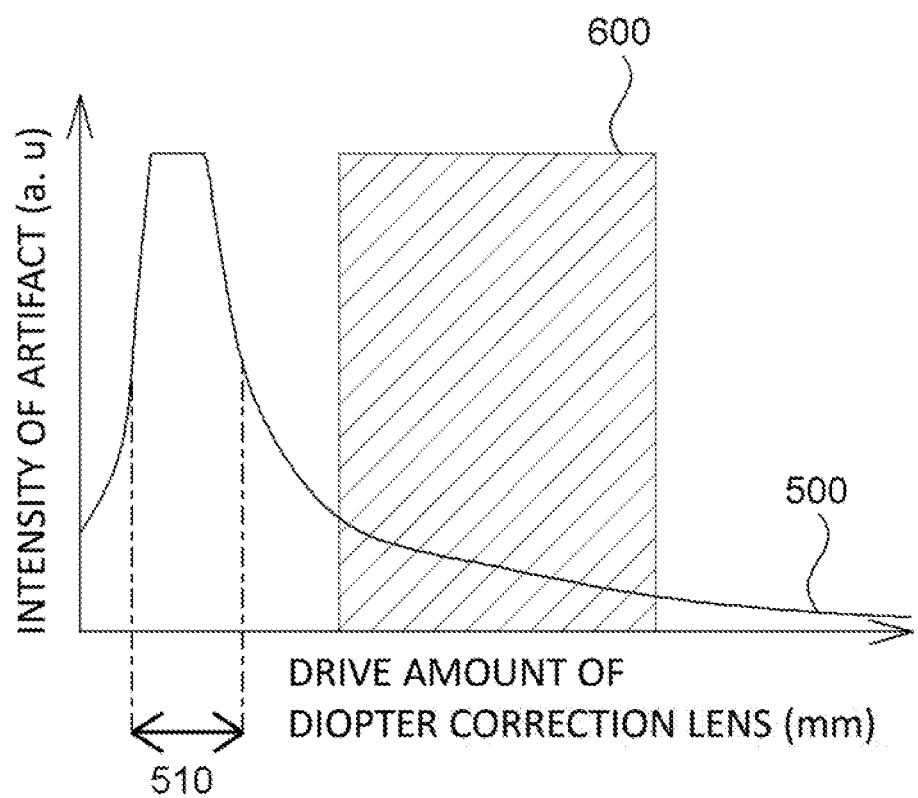
FIG. 3B is a graph showing a relationship between a drive range of the optical element in the diopter correction unit and an artifact in an inserted state.
Figure 5:
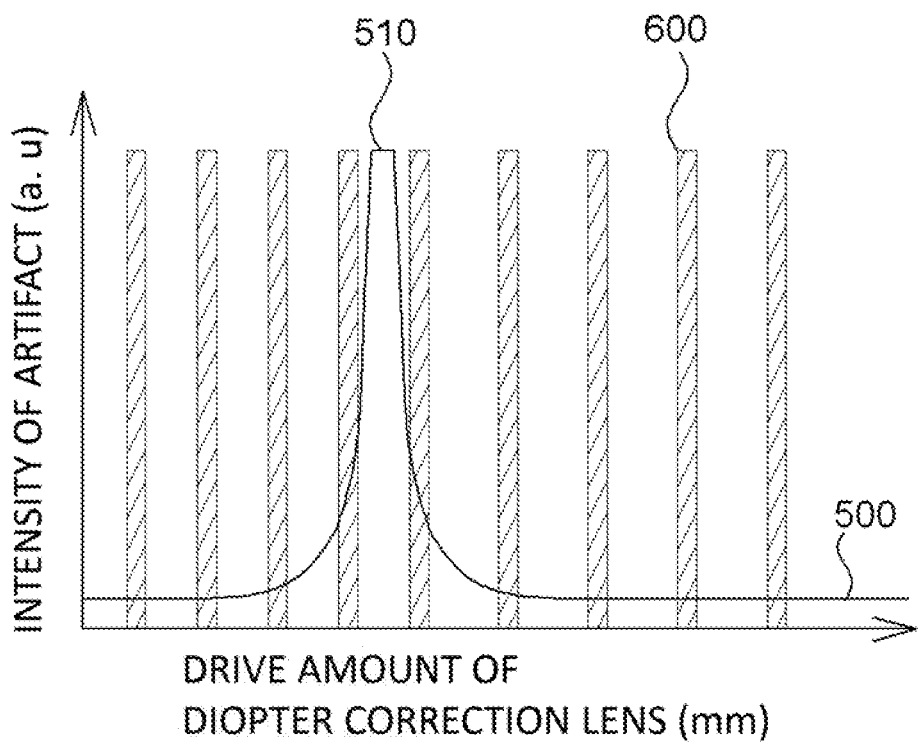
FIG. 5 is a diagram for describing a modification example of the present disclosure.

In FIGS. 3A, 3B, and 5, a waveform indicated by the reference numeral 500 indicates the intensity of the artifact. A range indicated by the reference numeral 510 is a peak portion.

The peak portion may be defined as appropriate depending on a shape of the waveform indicating the intensity of the artifact. In FIGS. 3B and 5, the peak portion includes at least a saturated range. In an example, the peak portion is a full width at half maximum of an intensity peak in the waveform indicating the intensity of the artifact. The peak portion may be a range in which the intensity is more than a predefined threshold value.

For example, in a case where a fundus image is captured at an angle of view of 70° or more, the peak portion may be formed toward a positive diopter side of +15 D or a negative diopter side of −15 D. For example, in a case where a fundus image is captured at an angle of view of 70° or more, the peak portion may be formed toward a negative diopter side of −10 D. The eye having a diopter value toward the negative diopter side of −10 D is called excessive myopia. In other words, the artifact may occur in a case where a subject eye is excessive myopia.

Unless otherwise mentioned, the intensity of the artifact in the present disclosure indicates a relative intensity with a fundus image.

As an angle of view becomes wider in capturing a favorable fundus image, the sensitivity of a spectrum interference signal is preferably improved. In order to improve the sensitivity of the spectrum interference signal, at least any of parameters related to the sensitivity, for example, an amount and an exposure time of light applied to the fundus and a gain in the light receiving element may be increased. For example, as an angle of view is increased, an area of the fundus required to be irradiated with light becomes wider, and thus contrast of a fundus image tends to deteriorate. In contrast, the deterioration in contrast is reduced by adjusting the parameters related to the sensitivity of the spectrum interference signal.

However, even though the sensitivity of the spectrum interference signal is increased, a relative intensity relationship between a fundus image and an artifact does not change. Therefore, as the sensitivity of the spectrum interference signal is increased, the intensity of the artifact is increased. In other words, the artifact tends to be problematic in an apparatus having a larger angle of view.

<Suppressing Artifact by Restricting Drive Range of Optical Element in Diopter Correction Unit>

In contrast, in the fundus imaging apparatus of the present embodiment, a drive range of the optical element in the diopter correction unit may be set to avoid the peak portion (refer to FIGS. 3B and 5). Consequently, an artifact based on reflection light in the objective lens is suppressed. In this case, a drive range of the optical element is set to avoid the peak portion by at least one of the objective lens system and the control unit. In the graphs in FIGS. 3A, 3B, and 5, a diagonally hatched range indicated by the reference numeral 600 is a drive range.

For example, the control unit may restrict the drive range to a range not overlapping at least the peak portion. The term "restriction" indicates that the optical element of the diopter correction unit is prohibited from being driven in a range except a defined drive range.

<Angle-of-View Switching Unit>

Here, angles of view of the imaging optical system may be switched by the angle-of-view switching unit. In the present embodiment, the angle-of-view switching unit may switch angles of view by changing a lens configuration of the objective lens system. In this case, an angle of view may be selectively switched to one of two predefined values by the angle-of-view switching unit. Of the two predefined values, a smaller angle of view will be referred to as a "first angle of view", and a larger angle of view will be referred to as a "second angle of view". For example, the first angle of view may be less than 70°, and the second angle of view may be equal to or more than 70°. For example, the first angle of view may be 45° to 60° and the second angle of view may be 70° to 150°.

The objective lens system may include a first lens system and a second lens system. In this case, the first lens system is fixed to the apparatus main body, and the second lens system is inserted and removed between the first lens system and a subject eye by the angle-of-view switching unit. In the present embodiment, a fundus image is captured at the first angle of view in a state (retreated state) in which the second lens system is retreated from between the first lens system and the subject eye. A fundus image is captured at the second angle of view in a state (inserted state) in which the second lens system is inserted between the first lens system and the subject eye. In the inserted state, reflection light directed toward the light receiving element is generated at a lens surface of each of the first lens system and the second lens system.

Here, in a case of the second angle of view (that is, the inserted state), light passes through both of the first lens system and the second lens system, and thus the number of optical elements through which the light passes is larger than in a case of the first angle of view (that is, the retreated state). Thus, in a case of the second angle of view, a loss of a light amount during each of light irradiation and light reception is greater than in a case of the first angle of view. Therefore, at the second angle of view, a fundus image tends to be darker than at the first angle of view. On the other hand, in a case where amounts of light from the light source are the same as each other between the first angle of view and the second angle of view, amounts of reflection light at any lens surface are the same as each other between the first angle of view and the first angle of view. In other words, in a case of the second angle of view, an amount of reflection light at the lens surface in a fundus image is relatively increased. Particularly, in this case, the influence of reflection light from the first lens system may be great.

Therefore, the control unit may restrict a drive range of the optical element in the diopter correction unit to a range not overlapping the peak portion related to the first lens system at the second angle of view (inserted state) (refer to FIGS. 3B and 5).

<Mode Changing Due to Angle-of-View Switching>

The control unit may change an imaging mode of the apparatus between a first mode and a second mode. The first mode is a mode in which the fundus is imaged at the first angle of view. The second mode is a mode in which the fundus is imaged at the second angle of view. The control unit may change, for example, an imaging condition and apparatus control according to an imaging mode.

In this case, the control unit may change a drive range of the optical element in the diopter correction unit between the first mode and the second mode. In other words, the control unit may change a drive range according to angle-of-view switching performed by the angle-of-view switching unit.

For example, the control unit may restrict a drive range of the optical element to a narrower range in the second mode than in the first mode. In this case, the control unit may restrict a drive range such that at least one of an upper limit and a lower limit of a diopter value corresponding to the drive range is smaller in the second mode than in the first mode. In an example, a drive range corresponding to +20 D may be set in the first mode, and a drive range corresponding to +15 D may be set in the second mode.

The optical element may be driven in steps such that a correction value in the diopter correction unit is stepwisely changed. In this case, for example, a diopter value is changed by skipping a predetermined value (for example, 0.5 D). In this case, a drive amount of the optical element in each step may be set such that the peak portion of an artifact is located between any two values separated by one step (refer to FIG. 5). In the present embodiment, particularly, a drive amount corresponding to each step in the second mode is preferably set to exclude a range corresponding to the peak portion.

<Fundus Conjugate Position Shift Using Second Lens System>

A drive range of the optical element may be set to avoid the peak portion in the inserted state by using the second lens system. For example, the second lens system may displace a fundus conjugate position (hereinafter, referred to as a first position for convenience) that is formed nearest the first lens system in the inserted state, to be separated from the first lens system in the retreated state. The first position may be a fundus conjugate position of a 0-D eye. The second lens system is formed by a parfocal optical system. In a case where a lens surface closest to a subject eye in the second lens system is formed to be concave, this is advantageous in shifting the fundus conjugate position.

However, this is only an example. In a case where an angle of view is increased by inserting the second lens system, a change of diopter (correction value) corresponding to a drive amount of the optical element in the diopter correction unit is increased in the inserted state more than in the retreated state. Thus, even though the first position in the inserted state is closer to the lens surface of the first lens system than in the retreated state, there may be a case where a drive range corresponding to a range of a desired diopter value is separated from the peak portion as a whole. As a result, an artifact may be easily suppressed in the inserted state.

A method of and means for switching angles of view in the imaging optical system are not limited to insertion and removal of the second lens system. For example, angles of view may be switched by replacing a part or the whole of the objective optical system. Angles of view may be switched by a zoom mechanism that changes placement of the optical elements of the objective optical system.

For example, in a case where a part or the whole of the objective optical system is replaced, a first objective lens system corresponding to the first angle of view and a second objective lens system corresponding to the second angle of view may be provided as objective lens systems disposed on the optical path, and either of the first objective lens system and the second objective lens system may be alternatively disposed on the optical path to switch the angle of view.

In this case, a fundus image is captured at the second angle of view in a state where the second objective lens system is disposed on the optical path. In this case, a drive range of the optical element in the diopter correction unit is preferably set to avoid the peak portion related to the second objective lens system.

<Control Operation in OCT>

In a case where the fundus imaging apparatus is an OCT apparatus, a light amount adjustment unit that changes an amount of reference light may be provided on a reference optical path. The light amount adjustment unit may be controlled by the control unit such that an amount of reference light may be changed according to a diopter value in at least the second mode.

The light amount adjustment unit may be, for example, an attenuator. Particularly, a variable attenuator that can change an attenuation factor of reference light may be used. An attenuator having a constant attenuation factor may be inserted into and removed from the reference optical path according to a diopter value such that an amount of reference light is adjusted.

The reference optical path may include a first reference optical path having an optical path length corresponding to the retreated state (first mode) and a second reference optical path having an optical path length corresponding to the inserted state (second mode). The attenuator may be disposed on the second reference optical path such that an artifact caused by reflection at the objective lens in the inserted state is prevented from being saturated.

EXAMPLE

Hereinafter, one typical Example of the present invention will be described with reference to the drawing. First, with reference to FIGS. 1 to 4, the overall configuration of a fundus imaging apparatus 1 will be described. In the present example, the fundus imaging apparatus 1 includes an OCT optical system 100 (refer to FIG. 1) that acquires OCT data of the fundus. In the present example, the OCT optical system 100 has, for example, a spectral domain type OCT (SD-OCT) as a fundamental configuration.

As illustrated in FIG. 2, the fundus imaging apparatus 1 includes a calculation controller (a calculation control unit; hereinafter, simply referred to as a control unit) 70. In addition, the fundus imaging apparatus 1 may include a memory 72, a monitor 75, an operation unit 80, and the like.

The calculation controller (hereinafter, a control unit) 70 is connected to an OCT light source 102, the OCT optical system 100, a driver 133a, and the like. The driver 133a is a part of the diopter correction unit, and drives a diopter correction lens 133 (refer to FIG. 1) on the basis of a control signal.

The operation unit 80 may be a touch panel, a mouse, and a keyboard. The operation unit 75 may be a device provided separately from the fundus imaging apparatus 1. The control unit 70 may control each unit on the basis of an operation signal output from the operation unit 80. For example, either of an operation for selecting an imaging mode and an operation for release may be input to the operation unit 80.

<OCT Optical System>

The OCT optical system 100 guides measurement light to an eye E by using a light guide optical system 130. The OCT optical system 100 guides reference light to a reference optical system 140. The OCT optical system 100 causes interference signal light acquired through interference between measurement light reflected by the eye E and reference light to a detector (light receiving element) 120. The OCT optical system 100 may be mounted in a casing (apparatus main body) (not illustrated), and may be aligned with the subject eye by three-dimensionally moving the casing with respect to the eye E via an operation member such as a joystick by using a well-known alignment movement mechanism.

An SD-OCT system is used for the OCT optical system 100. A light source that emits a light flux with a low coherent length is used as the OCT light source 102, and a spectroscopic detector that detects a spectrum interference signal through spectral diffraction for each wavelength component is used as the detector 120.

A coupler (splitter) 104 is used as a first light splitter, and splits light emitted from the OCT light source 102 into light directed toward a measurement optical path and light directed toward a reference optical path. The coupler 110 guides light from the OCT light source 102 to an optical fiber 112 on the measurement optical path side and also guides the light to the reference optical system 140 on the reference optical path side.

<Light Guide Optical System>

The light guide optical system 130 is provided to guide measurement light to the eye E. The light guide optical system 130 may be provided with, for example, the optical fiber 112, a collimator lens 131, a variable beam expander 132, a focusing lens 133, an optical scanner 134, and an objective lens 320 (the first objective lens system in the present example) in this order. In this case, the measurement light is emitted from an emission end of the optical fiber 112 and is then converted into a parallel beam by the collimator lens 131. Thereafter, the parallel beam is directed toward the optical scanner 134 through the focusing lens 133 in a state of having a desired a light flux diameter in the variable beam expander 132. The light having passed through the optical scanner 134 is applied to the eye E through the objective lens 320.

In the present example, the focusing lens 133 is displaced along an optical axis, and thus a diopter value to be corrected is changed.

A first turning point P1 is formed at a point conjugate to the optical scanner 134 with respect to the objective lens 320. The anterior ocular segment is located at the first turning point P1, and thus the measurement light reaches the fundus without eclipse. The fundus is scanned with the measurement light according to an operation of the optical scanner 134. In this case, the measurement light is scattered and reflected by tissue of the fundus.

In the present example, for convenience of description, the objective lens 320 is illustrated to be a single lens, but is not necessarily limited thereto, and may be a plurality of lenses.

In the reference sign Ic in FIG. 1 indicates a fundus conjugate position with respect to the objective lens 320.

The optical scanner 134 may scan the eye E with the measurement light in an XY direction (transverse direction). The optical scanner 134 is formed of, for example, two Galvano mirrors, and reflection angles thereof are adjusted to any angles by a drive mechanism. A light flux emitted from the OCT light source 102 is applied onto the fundus in any direction by changing a reflection (advancing) direction thereof. As the optical scanner 134, for example, not only a reflection mirror (Galvano mirror, a polygon mirror, or a resonant scanner) but also an acousto-optic modulator (AOM) that changes an advancing (refraction) direction of light may be used.

Scattered light (reflection light) from the eye E based on the measurement light advances on a path reverse to the path during transmission, and is incident to the optical fiber 112 to reach the coupler 110. The coupler 110 guides the light from the optical fiber 112 to the optical path directed toward the detector 120.

<Attachment Optical System>

In the OCT apparatus of the Example, an attachment optical system 330 (the second objective lens system in the present example) is inserted and removed between the objective lens 320 of the light guide optical system 130 and the subject eye E. In an example, a lens attachment including the attachment optical system 330 is attached to and detached from (inserted into and removed from) a casing surface (not illustrated), and thus the attachment optical system 330 is inserted and removed between the objective lens 320 on the apparatus main body side and the subject eye E.

The attachment optical system 330 may include a plurality of lenses 331 and 332. However, the attachment optical system is not necessarily limited thereto, and may include a single lens. At least the lens 164 bends the measurement light having passed through the first turning point P1 toward an optical axis L, and thus a second turning point P2 is formed at a position conjugate to the optical scanner 134 with respect to the attachment optical system 330 and the objective optical system 158. In other words, the attachment optical system 330 is an optical system that relays the turning point P1 to the turning point P2.

In the present example, an amount of the turning measurement light at the second turning point P2 is larger than an amount of the turning measurement light at the first turning point P1. For example, in a case where a turning amount is represented by a solid angle, a solid angle at the second turning point P2 is increased twice or more the solid angle at the first turning point P1. In the present example, scanning is possible in a range of about 60° in the retreated state (first mode), and scanning is possible in a range of about 100° in the inserted state (second mode).

In the present example, the attachment optical system 330 shifts the fundus conjugate position Ic to be more distant from the lens surface of the objective lens 320 on the light source side than in the retreated state.

The control unit 70 may be provided with an insertion/removal detection unit that automatically determines whether or not the attachment optical system 330 is inserted into the light guide optical system, and the control unit may execute control of each unit of the OCT optical system 100 and processes on the basis of a detection signal from the detection unit. In other words, the control unit 70 may change an imaging mode of the apparatus between the first mode and the second mode. The first mode is a mode in which the fundus is imaged at the first angle of view. The second mode is a mode in which the fundus is imaged at the second angle of view. The control unit 70 changes an imaging condition and apparatus control according to an imaging mode.

For example, as will be described later, restriction of a drive range of the focusing lens 133 in the diopter correction unit, control of changing a light flux diameter with using the variable beam expander 155, control of setting a zero delay position using a reference optical path adjustment unit 145, and a process of changing dispersion amounts in the optical systems between the measurement optical path and the reference light, which will be described later, may be executed as appropriate according to an imaging mode. As the insertion detection unit, a sensor disposed near the objective lens 320 may be used.

Of course, an examiner may input information for specifying a state (the inserted state or the retreated state of the attachment optical system) of the light guide optical system to a user interface (UI) of the OCT apparatus, and the control unit may execute control of each unit of the OCT optical system 100 and processes on the basis of the information.

Here, the control unit 70 of the present example changes a drive range (indicated by the reference numeral 600) of the focusing lens 133 as illustrated in FIGS. 3A and 3B between the first mode and the second mode. As described above, in FIGS. 3A and 3B, the intensity of an artifact is represented by a waveform indicated by the reference numeral 500, and the peak portion is indicated by the reference numeral 510. The drive range is a hatched range indicated by the reference numeral 600.

Figure 4:
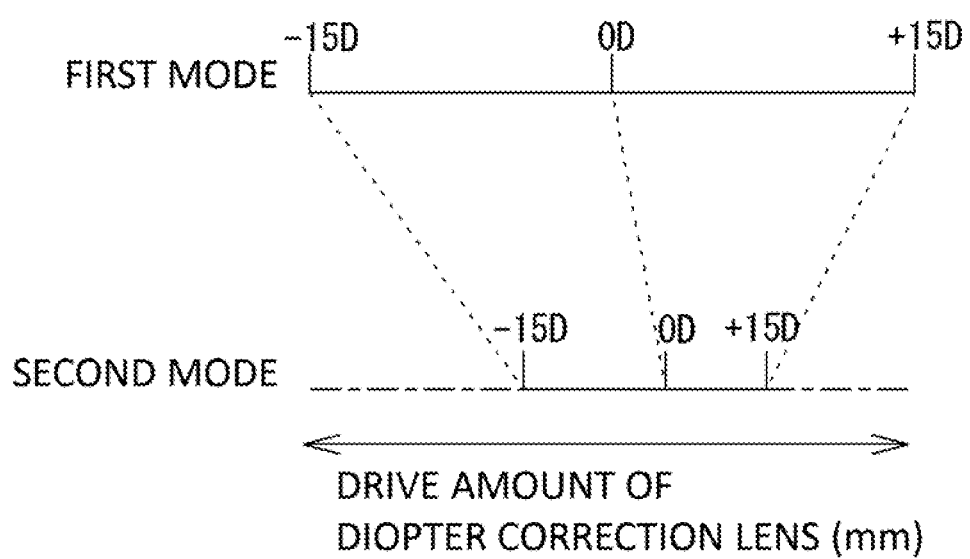
FIG. 4 is a diagram illustrating a correspondence relationship of a drive range in the diopter correction unit between the inserted state and the retreated state.

In the present example, a drive range in each of the first mode and the second mode corresponds to a diopter value from −15 D to +15 D. FIG. 4 illustrates a drive amount (movement amount) of the focusing lens corresponding to a correction value of +15 D in each of the first mode and the second mode. As illustrated in FIG. 4, an angle of view is larger in the second mode than in the first mode, and thus a range of a drive amount corresponding to the correction value of +15 D is narrower in the second mode than in the first mode. In other words, it can be seen that a change of a diopter value corresponding to a drive amount (a displacement amount of the focusing lens 133) of the driver 133a is increased more than in the first mode.

Therefore, as represented in the transition from FIG. 3A to FIG. 3B, a drive range of the focusing lens 133 is restricted to a narrower range in the second mode than in the first mode. Herein, in the second mode, a drive range is restricted to realize the same correction range (a range from −15 D to +15 D) of a diopter value as in the first mode.

In an example, FIGS. 3A and 3B illustrate a relationship between an artifact due to the objective lens 320 and a drive range of the focusing lens 133. In a case where the same drive range as in the first mode is assumed to be also set in the second mode, the peak portion (indicated by the reference numeral 510) of the artifact may overlap the drive range in the second mode. As described above, an angle of view is spread such that the intensity of the artifact is increased in the second mode more than in the first mode, and, as a result, saturation may occur in the peak portion in the second mode. In contrast, in the present example, in the second mode, a drive range is restricted to a range not overlapping the peak portion. As a result, it also becomes easier to capture a favorable image in which an artifact is suppressed even in the second mode.

The variable beam expander 132 is a light flux diameter adjustment unit in the Example. In an example, the variable beam expander 132 may have a plurality of lenses forming a both-side telecentric optical system, and may change light flux diameters by changing a lens gap with an actuator. The variable beam expander 132 adjusts a light flux diameter of measurement light on the basis of an instruction from the control unit 70.

Assuming that a light flux diameter of measurement light guided from the variable beam expander 132 to the optical scanner 134 is constant between the retreated state (first mode) and the inserted state (second mode), a spot size of the measurement light on the fundus is proportional to an angle of view, and thus a resolution is reduced in the inserted state more than in the retreated state. Therefore, in the present example, the control unit 70 drives the variable beam expander 132 according to insertion and removal of the attachment optical system, and thus reduces a light flux diameter in the inserted state more than in the retreated state. A ratio between light flux diameters (light flux diameters in the variable beam expander 132) in the inserted state and the retreated state is inversely proportional to a ratio between angles of view in the inserted state and the retreated state, and thus it is possible to suppress a change in a resolution based on insertion and removal of the attachment optical system 330.

<Reference Optical System>

The reference optical system 140 generates reference light to be combined with fundus reflected light of measurement light. The reference light having passed through the reference optical system 140 is combined with light from the measurement optical path to interfere with the light at a coupler 149. The reference optical system 140 may be of a Michelson type or a Mach-Zehnder type.

The reference optical system 140 illustrated in FIG. 1 is formed of a transmission optical system. In this case, the reference optical system 140 does not return light from the coupler 110 but transmits the light therethrough to be guided to the detector 120. The reference optical system 140 is not limited thereto, and may be formed of a reflection optical system, and may reflect light from the coupler 110 at the reflection optical system, to be guided to the detector 120.

In the present example, the reference optical system 140 may be provided with a plurality of reference optical paths. For example, in FIG. 1, the reference optical path is branched into an optical path (a first branched optical path in the present example) passing through a fiber 142 and an optical path (a second branched optical path in the present example) passing through a fiber 143 by a coupler 141. The fiber 142 and the fiber 143 are connected to a coupler 145 such that the two branched optical paths are coupled to each other, and thus light is incident to the coupler 149 through the reference optical path adjustment unit 147 and a polarization adjustment unit 148.

In the present example, the reference light from the coupler 110 is simultaneously guided to the fiber 142 and the fiber 143 by the coupler 141. Both of light having passed through the fiber 142 and light having passed through the fiber 143 are combined with the measurement light (fundus reflected light) in the coupler 149.

An optical path length difference between the fiber 142 and the fiber 143, that is, an optical path length difference between the first branched optical path and the second branched optical path may be a fixed value. In the present example, the optical path length difference is the substantially same as an optical path length of the attachment optical system 330.

The reference optical path adjustment unit 147 adjusting an optical path length difference between measurement light and reference light may be provided on at least either of the measurement optical path and the reference optical path. An adjustment range of an optical path length in the reference optical path adjustment unit 147 is preferably set to be sufficiently short with respect to an optical path length difference between the fiber 142 and the fiber 143 (in other words, an optical path length difference between the first branched optical path and the second branched optical path).

<Optical Detector>

The detector 120 is provided to detect interference between light from the measurement optical path and light from the reference optical path. In the present example, the detector 120 is a spectroscopic detector, and includes, for example, a spectroscope and a line sensor. Measurement light and reference light that are combined with each other by the coupler 149 are spectrally diffracted by the spectroscope and are received at different regions (pixels) of the line sensor for each wavelength. Consequently, an output from each pixel is acquired as a spectrum interference signal.

A curve of the fundus does not necessarily match an image forming surface of measurement light, and a difference between both thereof increases in at least one of a fundus central part and a fundus peripheral part in a state where the attachment optical system 150 is inserted. Therefore, a sufficient depth range is preferably secured in the optical detector by taking into consideration the difference.

<Acquisition of Depth Information>

The control unit 70 performs a process (Fourier analysis) on a spectrum interference signal detected by the detector 120 so as to obtain OCT data of the subject eye.

The spectrum interference signal (spectrum data) may be rewritten as a function of a wavelength λ, and may be converted into a function I(k) having an equal interval with respect to a wave number k (=2π/λ). Alternatively, the spectrum interference signal may be acquired as the function I(k) having an equal interval with respect to the wave number k from the beginning (K-CLOCK technique). The calculation controller may obtain OCT data in a depth (Z) region by performing Fourier transform on the spectrum interference signal in the space of the wave number k.

Information after the Fourier transform may be represented by a signal including a real number component and an imaginary number component in the Z space. The control unit 70 may obtain OCT data by obtaining absolute values of a real number component and an imaginary number component of a signal in the Z space.

Here, reference light having passed through the first branched optical path and reference light having passed through the second branched optical path are guided to the coupler 149 together, and each thereof is combined with measurement light. Since there is a great optical path length difference that is the substantially same as an optical path length of the attachment optical system 330 between the first branched optical path and the second branched optical path, one of the reference light having passed through the first branched optical path and the reference light having passed through the second branched optical path easily interferes with the measurement light, but the other thereof hardly interferes therewith. The spectrum interference signal from the detector 120 includes a component based on the reference light having passed through the first branched optical path and a component based on the reference light having passed through the second branched optical path, but only one of the two components corresponding to a state of the light guide optical system 130 is obtained as a remarkably stronger signal than the other component. As a result, favorable OCT data can be obtained regardless of a state of the light guide optical system 130. In other words, a plurality of reference optical paths having an optical path length difference corresponding to the attachment optical system 330 are provided, and thus the OCT apparatus according to the Example compensates for a change amount of an optical path length difference between the measurement optical path and the reference optical path, the change amount being caused by insertion and removal of the attachment optical system 330, regardless of a state of the light guide optical system 130.

An optical path length difference between the measurement optical path and the reference optical path and regarding an eye axis length of the subject eye E may be further adjusted by controlling the reference optical path adjustment unit 147.

In the inserted state, since fundus reflected light of measurement light from the fundus peripheral part is weaker than reflection light from the fundus central part, an optical path length difference between the measurement optical path and the reference optical path may be adjusted by the reference optical path adjustment unit 147 such that a zero delay position between the measurement optical path and the reference optical path overlaps desired fundus tissue (for example, the retina, the choroid, or the sclera) in the fundus peripheral part.

In the example illustrated in FIG. 1, the fiber 143 is connected to an attenuator 143a. The attenuator 143a is disposed to adjust a light amount balance between measurement light and reference light in the inserted state and the retreated state of the attachment optical system 330. An attenuation factor in the attenuator 143a may be set as appropriate in a range in which an artifact caused by the objective lens 320 is sufficiently suppressed. As illustrated in FIG. 1, in a case where the attenuator is disposed on the branched optical path in the reference optical system, an attenuation factor in the attenuator may be constant.

The attenuator may be disposed at a location other than the branched optical path in the reference optical system. In this case, an attenuation factor in the attenuator may be variable, and attenuation factors may be switched by the control unit 70 between the inserted state and the retreated state of the attachment optical system 330. In this case, an attenuation factor in the attenuator may be adjusted and controlled according to a drive amount of the focusing lens 133 such that the luminance of an artifact caused by the objective lens 320 is not saturated.

In the detector 120, a gap between a grading element 121 (for example, a diffraction grating or a grading lens) and a line sensor 122 may be changeable, and a range of light (here, light obtained by combining measurement light with reference light) applied to all pixels of the line sensor may be changed by changing the gap. Consequently, resolutions in a depth direction can be changed. For example, an irradiation range in the line sensor 122 may be increased in the inserted state more than in the retreated state. Consequently, OCT data at each position in the fundus can be favorably acquired even in the inserted state.

In a case where A-scan is performed at an equal angular interval centering on the pupil, a density of scan points on the fundus may be higher on the fundus peripheral side than in the fundus central part. In the retreated state, there is no great difference among distances from the turning point to respective scan points, and thus the scan points are located at substantially equal intervals, but, in the inserted state, the density that cannot be ignored may occur. Therefore, in the inserted state, an angle interval centering on the turning point and of A-scan for the fundus central part may be set to denser than an angle interval of A-scan for the fundus peripheral part. Consequently, positions where OCT data of the fundus is acquired can be more uniformly set in the inserted state.

In the present example, a dispersion amount difference in the optical systems between the measurement optical path and the reference light is corrected through signal processing. Specifically, the signal processing is performed by applying a correction value stored in a memory in advance to processing of the spectrum interference signal. In the present example, a first correction value corresponding to the retreated state and a second correction value that is different from the first correction value and corresponds to the inserted state are stored in the memory 71 in advance, and a correction value to be applied is changed according to a state of the light guide optical system. As a result, the OCT apparatus according to the Example compensates for a change amount of a dispersion amount between the measurement optical path and the reference optical path, the change amount being caused by insertion and removal of the attachment optical system 330, according to each state of the light guide optical system 130. However, a dispersion amount is not necessarily required to be corrected through signal processing, and may be corrected by inserting and removing an optical element for dispersion correction into and from a transmission and reception optical path for measurement light.

The polarization adjustment unit 148 adjusts a state of polarization (herein, a state of polarization of reference light). The state of polarization may be switched according to states of attachment and detachment (insertion and removal) of the attachment optical system 330. For example, the state of polarization may be changed by driving the polarization adjustment unit 148 by a predefined angle before and after attachment or detachment (insertion or removal) of the attachment optical system 330.

Modification Example

In the above description, the Example of SD-OCT has been described, but this is only an example, and the present example may be applied to SS-OCT.

What is claimed is:

1. A fundus imaging apparatus comprising:
an imaging optical system that irradiates a fundus of a subject eye with light through an objective lens system, and enables to capture a fundus image of the subject eye based on return light from the subject eye; and
a diopter correction unit that includes an optical element disposed on an optical path of the imaging optical system and a drive unit driving the optical element, and performs a diopter correction with a diopter value corresponding to a drive amount of the optical element,
a control unit that controls a driving of the optical element,
an angle-of-view switching unit that switches an angle of view in the imaging optical system between a first angle of view and a second angle of view larger than the first angle of view by changing the objective lens system,
wherein a drive range of the optical element in the diopter correction unit is set to avoid a specific range being a range in which an artifact caused by reflection light in the objective lens system is maximized, and
wherein the control unit changes the drive range according to a switching of the angle of view performed by the angle-of-view switching unit.

2. The fundus imaging apparatus according to claim 1, wherein the control unit restricts the drive range to be disposed on a high diopter side or on a low diopter side with respect to the specific range.

3. The fundus imaging apparatus according to claim 1, wherein in a case where an imaging is performed at the second angle of view, the control unit restricts the drive range to a narrower range than a case where an imaging is performed at the first angle of view.

4. The fundus imaging apparatus according to claim 1, wherein the control unit drives the optical element in steps such that a diopter value corrected by the diopter correction unit is stepwisely changed, and
a drive amount of the optical element in each step is defined such that the specific range is located between any two values separated by one step.

5. A fundus imaging apparatus comprising:
an imaging optical system that irradiates a fundus of a subject eye with light through an objective lens system, and enables to capture a fundus image of the subject eye based on return light from the subject eye; and
a diopter correction unit that includes an optical element disposed on an optical path of the imaging optical system and a drive unit driving the optical element, and performs a diopter correction with a diopter value corresponding to a drive amount of the optical element,
a first objective lens system included in the objective lens system; and
an angle-of-view switching unit that has a second objective lens system, and inserts and removes the second objective lens system between the first objective lens system and a subject eye to switch an angle of view in the imaging optical system to a first angle of view in a retreated state of the second objective lens system and to a second angle of view larger than the first angle of view in an inserted state of the second objective lens system,
wherein a drive range of the optical element in the diopter correction unit is set to avoid a specific range being a range in which an artifact caused by reflection light in the objective lens system is maximized, and
wherein the second objective lens system in the inserted state sets the drive range to avoid the specific range related to the first objective lens system.

6. The fundus imaging apparatus according to claim 5, wherein the second objective lens system causes a fundus conjugate position closest to the first objective lens system to be more distant from the objective lens system in a case of the second angle of view than in a case of the first angle of view.

7. The fundus imaging apparatus according to claim 6, wherein a lens surface of the second objective lens system, which is disposed closest to a subject eye, is a convex surface.

8. The fundus imaging apparatus according to claim 5, wherein the control unit restricts the drive range to be disposed on a high diopter side or on a low diopter side with respect to the specific range.

9. The fundus imaging apparatus according to claim 5, wherein the control unit drives the optical element in steps such that a diopter value corrected by the diopter correction unit is stepwisely changed, and
a drive amount of the optical element in each step is defined such that the specific range is located between any two values separated by one step.

10. A fundus imaging apparatus comprising:
an imaging optical system that irradiates a fundus of a subject eye with light through an objective lens system, and enables to capture a fundus image of the subject eye based on return light from the subject eye; and
a diopter correction unit that includes an optical element disposed on an optical path of the imaging optical system and a drive unit driving the optical element, and performs a diopter correction with a diopter value corresponding to a drive amount of the optical element,
a light amount adjustment unit provided on the reference optical path to change an amount of the reference light; and
a first control unit that changes the amount of the reference light according to a drive amount of the optical element,
wherein a drive range of the optical element in the diopter correction unit is set to avoid a specific range being a range in which an artifact caused by reflection light in the objective lens system is maximized, and
wherein the imaging optical system includes:
a light splitter that splits light from an OCT light source into light directed toward a measurement optical path and light directed toward a reference optical path; and
an optical detector that detects a spectrum interference signal between measurement light guided to a fundus of the subject eye through the measurement optical path and reference light from the reference optical path.

11. The fundus imaging apparatus according to claim 10, wherein the objective lens system includes at least a first objective lens system,
the fundus imaging apparatus comprises an angle-of-view switching unit that inserts and removes a second objective lens system between the first objective lens system and a subject eye to switch an angle of view in the imaging optical system to a first angle of view in a retreated state of the second objective lens system and to a second angle of view larger than the first angle of view in an inserted state of the second objective lens system, and
the reference optical path includes:
a first reference optical path that has an optical path length corresponding to the retreated state of the second objective lens system;
a second reference optical path that has an optical path length corresponding to the inserted state of the second objective lens system; and
an optical attenuator disposed on the second reference optical path to suppress an artifact based on reflection light in the first objective lens system in the inserted state.

12. The fundus imaging apparatus according to claim 11, comprising:
a second control unit that changes a parameter related to a sensitivity of the spectrum interference signal between a case where a fundus is imaged at the first angle of view and a case where a fundus is imaged at the second angle of view,
wherein the optical attenuator has an attenuation factor corresponding to the parameter in a case of imaging at the second angle of view.

* * * * *